(12) United States Patent
Lococo

(10) Patent No.: US 10,561,500 B2
(45) Date of Patent: Feb. 18, 2020

(54) BONE IMPLANT

(71) Applicant: Stemmed Implant Technology Inc., St. Catherines (CA)

(72) Inventor: Michael Lococo, Niagara Falls (CA)

(73) Assignee: Stemmed Implant Technology Inc., St. Catherines (CA)

( * ) Notice: Subject to any disclaimer, the term of this patent is extended or adjusted under 35 U.S.C. 154(b) by 0 days.

(21) Appl. No.: 15/710,536

(22) Filed: Sep. 20, 2017

(65) Prior Publication Data

US 2018/0133013 A1  May 17, 2018

Related U.S. Application Data

(63) Continuation of application No. 14/959,594, filed on Dec. 4, 2015, now abandoned.

(60) Provisional application No. 62/087,665, filed on Dec. 4, 2014.

(51) Int. Cl.
| | |
|---|---|
| *A61F 2/28* | (2006.01) |
| *A61F 2/30* | (2006.01) |
| *A61C 8/00* | (2006.01) |
| *A61F 2/36* | (2006.01) |

(52) U.S. Cl.
CPC .............. *A61F 2/28* (2013.01); *A61C 8/0043* (2013.01); *A61F 2/30* (2013.01); *A61F 2/30734* (2013.01); *A61F 2/30749* (2013.01); *A61F 2/3601* (2013.01); *A61F 2002/3021* (2013.01); *A61F 2002/30738* (2013.01); *A61F 2002/30774* (2013.01); *A61F 2002/30878* (2013.01);

(Continued)

(58) Field of Classification Search
CPC ........ A61F 2/30728; A61F 2002/30738; A61F 2002/3404; A61C 8/0039
See application file for complete search history.

(56) References Cited

U.S. PATENT DOCUMENTS

| | | | |
|---|---|---|---|
| 4,936,856 A * | 6/1990 | Keller | A61F 2/30721 623/22.36 |
| 5,282,864 A | 2/1994 | Noiles et al. | |
| 5,549,692 A | 8/1996 | Sulzer et al. | |

(Continued)

FOREIGN PATENT DOCUMENTS

| | | | |
|---|---|---|---|
| FR | 2674122 A1 * | 9/1992 | ......... A61B 17/1721 |
| FR | 2990844 A1 | 11/2013 | |

OTHER PUBLICATIONS

Translation of FR2674122A1 retrieved from espacenet on Mar. 2, 2019. (Year: 2019).*

*Primary Examiner* — Megan Y Wolf
(74) *Attorney, Agent, or Firm* — Wolf, Greenfield & Sacks, P.C.

(57) ABSTRACT

Provided is an implant receiving apparatus (10) comprising a core (20), the core defining a first end (30) and a second end (40), a wall (50) comprising inner surface (60) and outer surface (70) and a centerline (80) extending centrally of and between the ends (30, 40), the size and shape of the core (20) defining a socket or cavity (90) adapted to receiving an implant engaging member (100), wherein the wall comprises at least one threaded bore (110) for engaging a screw retainer, the bore traversing through the wall from the inner surface to the outer surface. Also provided is an implant engaging member, an implant system comprising both an implant engaging member and implant receiving apparatus as well as kits comprising an implant receiving apparatus.

12 Claims, 8 Drawing Sheets

(52) U.S. Cl.
CPC .............. *A61F 2002/30904* (2013.01); *A61F 2220/0008* (2013.01)

(56) References Cited

U.S. PATENT DOCUMENTS

| | | | |
|---|---|---|---|
| 8,585,770 B2 * | 11/2013 | Meridew | A61F 2/30724 623/22.11 |
| 2004/0220673 A1 | 11/2004 | Pria et al. | |
| 2005/0159814 A1 * | 7/2005 | Karahalios | A61F 2/44 623/17.11 |
| 2016/0158015 A1 | 6/2016 | Lococo | |

\* cited by examiner

BONE IMPLANT

RELATED APPLICATIONS

This application is a continuation of and claims priority under 35 U.S.C. § 120 to U.S. Patent Application, U.S. Ser. No. 14/959,594, filed Dec. 4, 2015, which claims priority under 35 U.S.C. § 119(e) to U.S. Provisional Applications, U.S. Ser. No. 62/087,665, filed on Dec. 4, 2014, which is incorporated herein by reference.

FIELD OF INVENTION

The present invention relates to bone implants.

BACKGROUND OF THE INVENTION

It is known to provide various types of bone implants used in dentistry, joint prostheses installation or other branches of medicine. In most cases, the bone implant is used as an anchor in the bone for an extension secured to the top surface of the implant. A typical example of such implant is presented by implants used in dentistry but the present invention is not limited to that particular field of medicine. The known bone implants are of two basic types. First, an implant is simply screwed into a pre-drilled bore by self-tapping action during which the thread of the implant taps into the surrounding bone often causing substantial damage to the bone tissue surrounding the implant and thus retarding the healing process. Another implant, used often in installation of the artificial joint head to a femur, is simply an elongated, slightly tapered stem driven by impact force into the marrow of the femur destroying a considerable part of the marrow. It is also known to provide what basically amounts to a bolt-and-nut securement of the implant used in supporting the head of an artificial hip joint. Such arrangement again uses a considerable space and its installation often results in substantial destruction of the bone and marrow tissue in the vicinity of the implant.

There is a need in the art for novel bone implants. There is also a need in the art to provide a bone implant which would provide a firm attachment to the bone tissue without subjecting the bone or the marrow to undue damage caused by the installation process. Further there is a need in the art for implants that can be affixed into bone, particularly, the long axis of bones in a manner that is minimally invasive and/or damaging to the bone.

SUMMARY OF THE INVENTION

The present invention relates to bone implants.

According to the present invention there is provided an implant receiving apparatus comprising a core, the core defining a first end and a second end, a wall comprising inner surface and outer surface and a centerline extending centrally of and between the ends, the size and shape of the core defining a socket or cavity adapted to receiving an implant engaging member, wherein the wall comprises at least one threaded bore for engaging a screw retainer, the bore traversing through the wall from the inner surface to the outer surface.

Also provided by the present invention is an apparatus as described herein, wherein the wall is cylindrical, multilateral, frustoconical, oval or lemniscate in cross-sectional or three dimensional shape.

In a further embodiment, the apparatus comprises a wall, wherein the wall comprises two or more threaded bores.

In a further embodiment, the apparatus comprising at least one threaded bore comprises a threaded bore positioned in a upper portion of the wall closer to the first end than the second end of the implant receiving apparatus.

Also provided by the present invention, there is provided an apparatus as described herein, wherein the one or more threaded bores are positioned in the wall at an angle to permit a screw retainer to be threaded into the threaded bore along the axis thereof without interference from the wall or any other surface of the implant.

The present invention also provides an implant receiving apparatus as described herein wherein the inner surface of the wall comprises a projection, the threaded core traversing through at least part of the projection. Also contemplated are embodiments wherein the threaded core traverses through all of the projection.

In a further embodiment, there is provided the implant receiving apparatus as described herein, wherein the surface of the projection comprises a groove allowing a screw head to be tightened flush with the projection surface.

Also provided is an implant receiving apparatus as described herein, wherein the outer surface of the wall comprises a plurality of steps, back-biting fins or extensions which resist removal of the apparatus during and/or after implantation.

Also provided is an implant receiving apparatus as described herein, further comprising an implant engaging member attached thereto.

In a further embodiment, the present invention provides an implant receiving apparatus further comprising one or more screws sized to threadedly engage the threaded bore.

The present invention also provides an implant receiving system comprising the implant receiving apparatus as described herein and an implant engaging member. Further, the implant receiving system may further comprise one or more screws which are preferably medical grade.

According to a further embodiment of the present invention, there is provided an implant receiving apparatus comprising a core, the core defining a funnel and a canal, the canal extending from the centre of the funnel. The funnel and the canal are defined by a wall comprising inner surface and outer surface and a centerline extending centrally of and between the funnel and canal, the size and shape of the core defining a cavity to receive an implant engaging member, wherein the wall comprises at least one threaded bore for engaging a screw retainer, the bore traversing through the wall from the inner surface to the outer surface.

Also provided by the present invention is an apparatus wherein the wall is cylindrical, multilateral, frustoconical, oval or lemniscate in shape.

In a further embodiment, the apparatus comprises a wall, wherein the wall comprises two or more threaded bores.

Also provided by the present invention is an apparatus as described herein, wherein the one or more threaded bores are positioned in the wall at an angle to permit a screw retainer to be threaded into the threaded bore along the axis thereof without interference from the wall or any other surface of the implant.

In a further embodiment of an apparatus as described herein, the one or more threaded bores are positioned perpendicular to the wall.

In a further embodiment of an apparatus as described herein, one of the one or more threaded bores is positioned parallel to the centerline and the other of the one or more threaded bores is positioned perpendicular to the wall.

Also provided is an implant receiving apparatus as described herein, further comprising an implant engaging member attached thereto.

Also provided is an implant receiving apparatus as described herein, further comprising one or more screws sized to threadedly engage the threaded bore.

The present invention also provides an implant receiving system comprising the implant receiving apparatus as described herein and an implant engaging member. Further, the implant receiving system may further comprise one or more screws which are preferably medical grade.

In a further embodiment, the present invention provides a kit comprising an implant receiving apparatus and one or more:
a) implant engaging members;
b) stints;
c) drill bits;
d) medical grade screws;
e) directions for implanting the implant receiving apparatus and/or the implant engaging member;
f) glue, cement, or any other component for affixing the implant engaging member to the implant receiving apparatus,
or any combination of a)-f).

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

The following description is of an embodiment which is not meant to be limiting in any manner.

Figure 1:
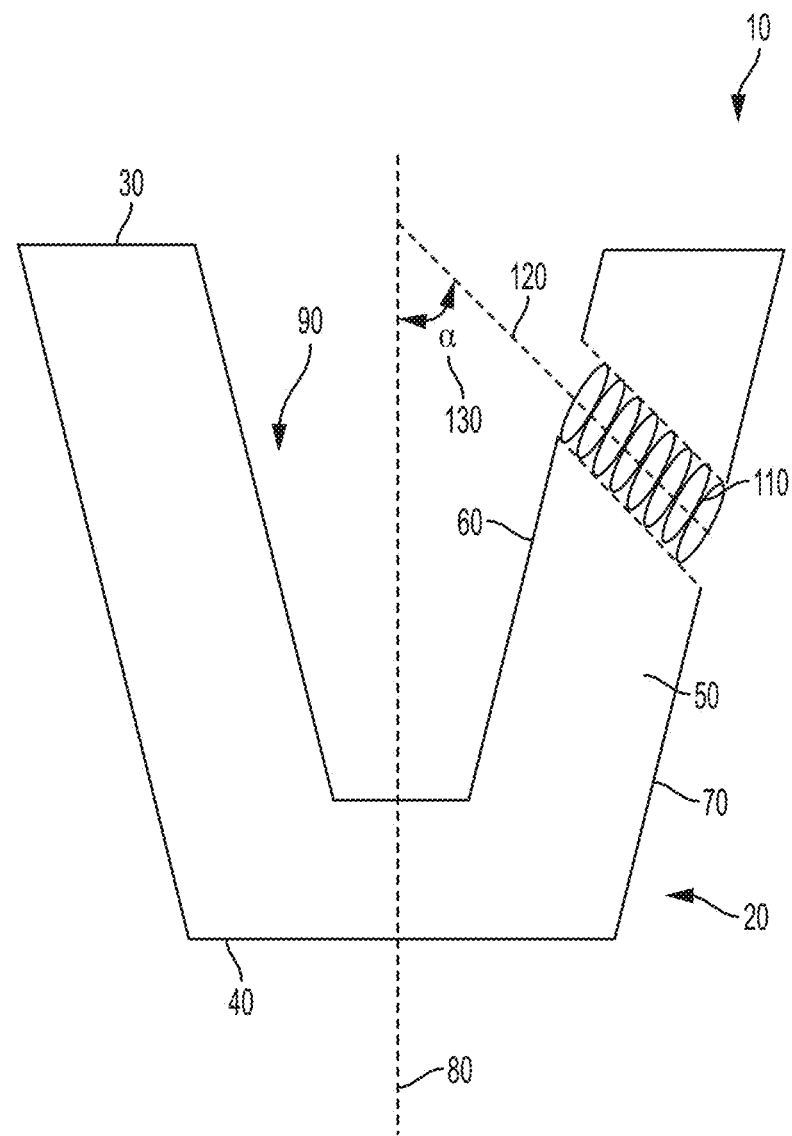
FIG. 1 shows aspects of a cross section of the implant receiving apparatus (10) comprising a core (20), first end (30), second end (40), wall (50), inner surface (60), outer surface (70), socket or cavity (90), threaded bore (110), long axis projection of threaded bore (120), angle α (130) formed by long axis projection of threaded bore (110) and centerline (80).

According to a first embodiment, and referring to FIG. 1, there is provided an implant receiving apparatus (10) comprising a core (20), the core defining a first end (30) and a second end (40), a wall (50) comprising inner surface (60) and outer surface (70) and a centerline (80) extending centrally of and between the ends (30, 40), the size and shape of the core (20) defining a socket or cavity (90) adapted to receive an implant engaging member (not shown), wherein the wall comprises at least one threaded bore (110) for engaging a screw retainer, the bore traversing through the wall from the inner surface to the outer surface.

Figure 2:
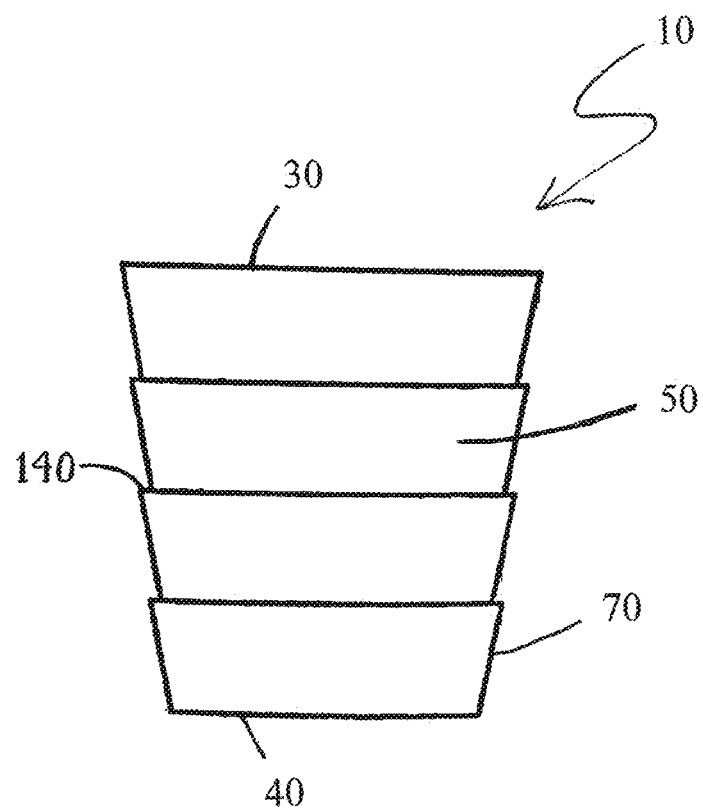
FIG. 2 shows aspects of a side profile of a representative implant receiving apparatus (10) comprising first end (30), second end (40), wall (50) and outer surface (70) showing a plurality of back biting fins or projections (140).
Figure 3:
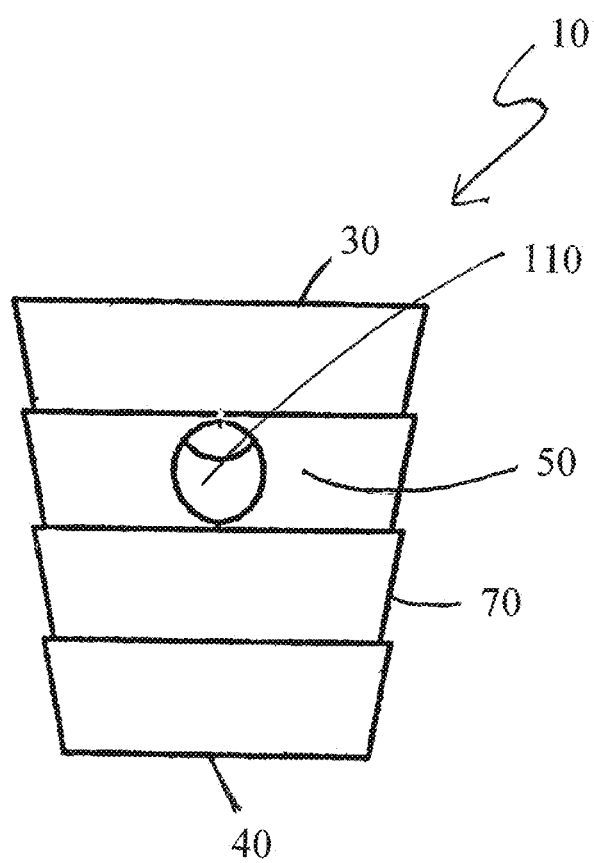
FIG. 3 shows aspects of a side profile of a representative implant receiving apparatus (10) that is at right angles to the embodiment shown in FIG. 2. The apparatus (10) comprises first end (30), second end (40), wall (50) and outer surface (70). Also shown is the threaded bore (110) in the wall.
Figure 4:
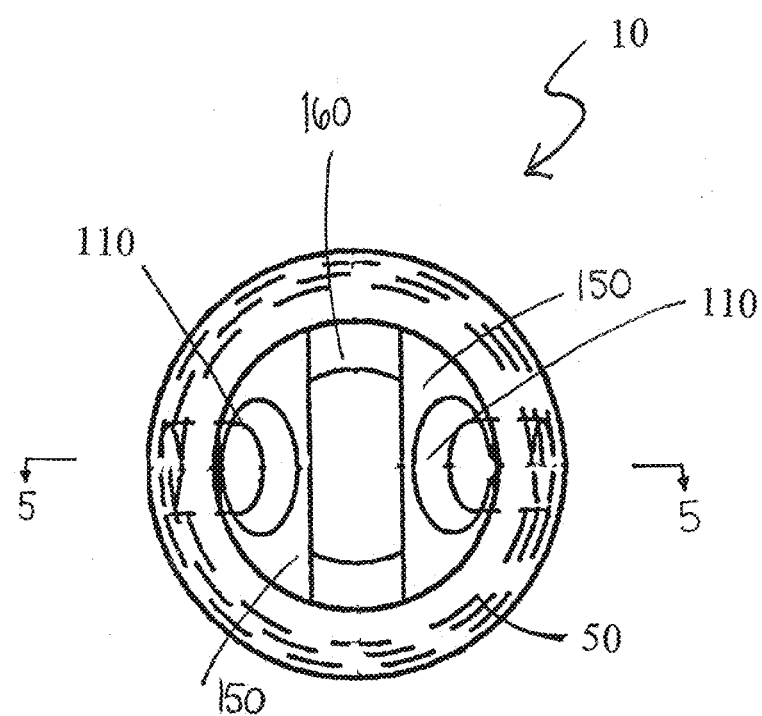
FIG. 4 shows aspects of a top view of a representative implant receiving apparatus (10) comprising wall (50), projection (150) on inner surface comprising threaded bore (110). Also shown is a slot (160) formed in the socket or cavity by projections (150).
Figure 5:
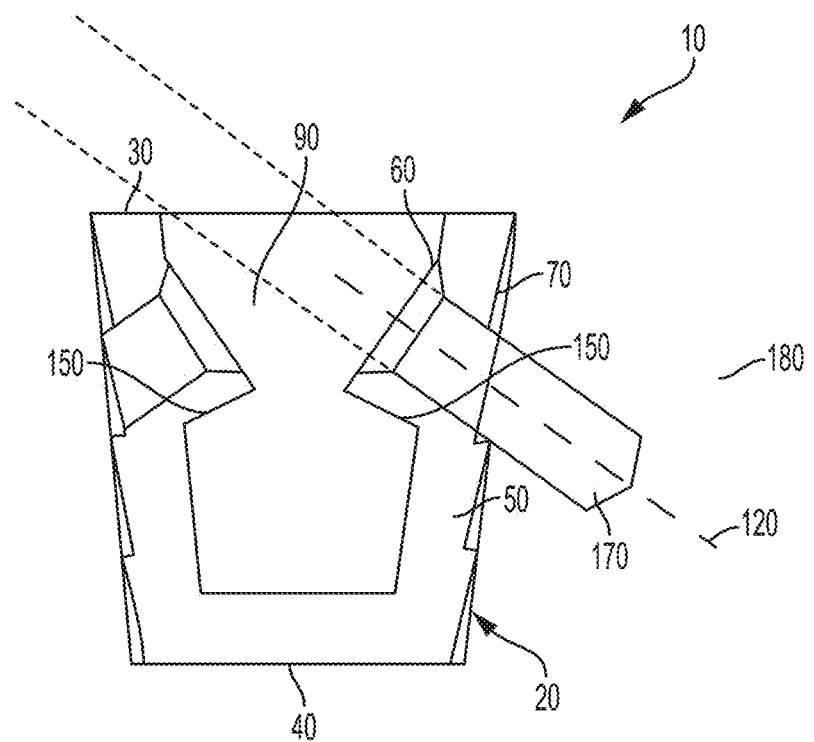
FIG. 5 shows aspects of a cross section of a representative implant receiving apparatus (10) comprising core (20), first end (30), second end (40), wall (50), inner surface (60), outer surface (70), socket or cavity (90), projections (150) and medical grade screw (170) inserted via threaded bore and extending into bone (180).
Figure 6:
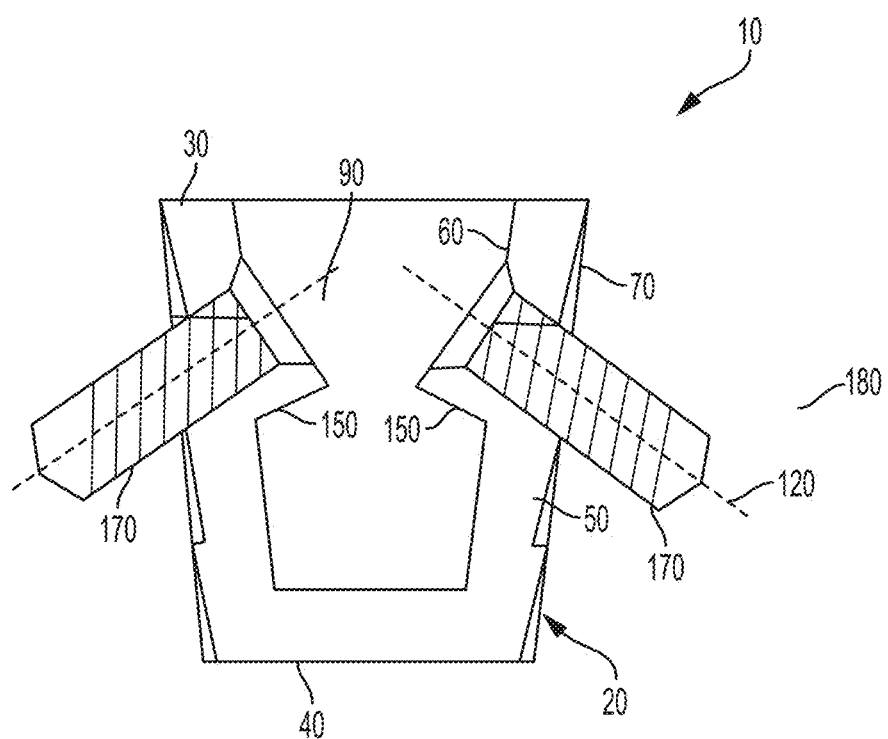
FIG. 6 shows further aspects of a cross section of a representative implant receiving apparatus (10) comprising core (20), first end (30), second end (40), wall (50), inner surface (60), outer surface (70), socket or cavity (90), projections (150) and medical grade screws (170) via threaded bore extending into bone (180). Screw thread lines are depicted to better show the screws in relation to the apparatus.

FIG. 2 illustrates a side view of an embodiment of an implant receiving apparatus wherein the threaded bore is at the back (not shown). The outer surface (70) illustrates a plurality of back biting fins or projections (140). The back biting fins permit a firm attachment of the implant receiving apparatus in the bone and resist removal of the apparatus during or after implantation. FIG. 3 illustrates a side view of an embodiment of an implant receiving apparatus comprising a threaded bore (110).

The present invention also contemplates an implant system comprising the implant receiving apparatus as described herein and an implant engaging member (not shown) that attaches to the implant receiving apparatus.

In an embodiment, the implant receiving apparatus, implant engaging member or both is made in part or in whole of titanium or any other material suitable for the purpose. However, the implant receiving apparatus and the implant engaging member may comprise different materials as required or desired. In a preferred embodiment, the implant receiving apparatus and implant engaging member are employed as a dental implant device, but it will be appreciated that applications other than dental applications may exist.

As discussed, the implant receiving apparatus (10) includes a core (20). The core (20) defines a first end (30), a second end (40) and a centerline (80) extending centrally of and between the ends. The wall (50) may be parallel to centerline or may be at an angle thereto. Thus, it follows that implant receiving apparatus may be cylindrical in shape, for instance, having a circular cross-section, but other shapes for example, but not limited to, oval, multilateral, frustoconical, lemniscate (figure-eight) cross-sectional and other volume-based configurations are also possible.

The implant receiving apparatus comprises at least one threaded bore. In a preferred embodiment, the apparatus comprises two or more threaded bores. More preferably, apparatus comprises two threaded bores positioned in the wall at opposite sides of the centerline, the threaded bores permitting a screw (170) or the like to be threaded from the exterior of the apparatus, via the cavity, through the inner surface of the wall, with a portion of the screw exiting the outer surface of the wall of the apparatus. During use, it is preferred that the screw is threaded into bone following exit from the outer surface of the wall of the apparatus to secure the implant receiving apparatus to the bone. When two or more screws are employed, the apparatus is fixed or locked into the bone and resists twisting, torquing, pulling, pushing forces and the like which would serve to easily unseat a non-fixed implant receiving apparatus. Further, by employing two threaded bores in the implant receiving apparatus as described, an implant can be affixed into the long axis of a bone and the direction of the screws permits greater penetration of the screw and reduces the chances of bone perforation. In a particularly preferred embodiment, the apparatus is positioned so that the screw placements are directed into the long axis of the jaw bone.

In a further embodiment, which is not meant to be considered limiting in any manner, the at least one threaded bore is formed in a upper portion of the wall closer to the first end than the second end of the implant receiving apparatus. This permits greater flexibility in the thickness and length of the screw retainer, as longer, thicker screws may be more difficult to thread through a bore located closer to the second end of the core as opposed to the first end due to clearance issues that may be present in apparatuses of certain shapes and dimensions, particularly apparatuses which have small sockets or cavities.

In general, it is preferred that the one or more threaded bores are positioned in the wall at an angle relative to the centerline to permit a screw retainer to be threaded into the threaded bore along the axis thereof without interference from any wall or surface of the implant as represented by angle α (130) in FIG. 1.

The angle formed between the axis of the threaded bore and the centerline is between zero and 90 degrees, preferably between 35 and 55 degrees, for example, but not limited to 35, 36, 37, 38, 39, 40, 41, 42, 43, 44, 45, 46, 47, 48, 49, 50, 51, 52, 53, 54 and 55 degrees. However, other angles including angles between the values listed above are also contemplated. Further, the angle may be defined by a range of any two of the values listed above. In embodiments wherein a plurality of threaded bores are employed, the bores may form the same or different angles with the centerline. Also possible, it is contemplated that a plurality of threaded bores may be positioned at different levels or depths in the wall or walls of the implant receiving apparatus.

In a further embodiment, the apparatus as described herein comprises a projection (150) of the inner surface of the wall associated with each of the threaded bores, the threaded bore traversing through at least part, but preferably all of the projection. More preferably, the threaded bore passes through the middle of the projection. Such projections may be employed to reduce the angle between the long axis of the threaded bore and the centerline of the apparatus as a screw or the like is inserted, thereby improving clearance for the screws. Such embodiments also direct the screw into bone in a more proximal position relative to the apparatus which be beneficial if more distal regions of the bone are weak and/or damaged. It is also contemplated that the projection further comprises a recessed groove which permits a screw head or the like to remain flush with the projection when fully tightened.

The implant engaging member may engage the implant receiving apparatus in a variety of ways, for example, but not limited to, the implant receiving apparatus may comprise a further threaded bore in a wall or surface of the cavity which permits the implant engaging member to be screwed into it. Alternatively, the implant receiving apparatus may comprise an extension or the like, for example, but not limited to a threaded post which may engage a threaded bore in the implant engaging member. Also possible, the implant engaging member may be sized to fit into the cavity of the implant receiving apparatus and the engaging member may be cemented, glued or otherwise affixed in place. As a further possibility, but not wishing to be limiting in any manner, the implant engaging member may comprise a portion which permits snap-fit attachment to the implant receiving apparatus. Combination of the above are also contemplated herein.

Figure 7:
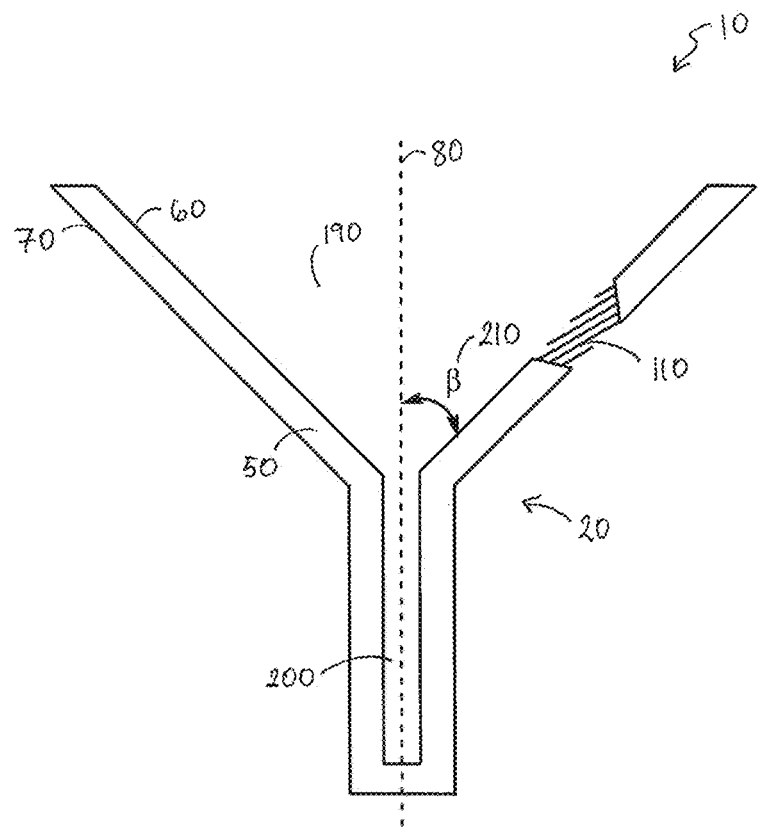
FIG. 7 shows aspects of a cross section of an implant receiving apparatus (10) comprising a core (20), a funnel (190), a canal (200) extending from the centre of the funnel (190), a wall (50) comprising inner surface (60) and outer surface (70), a centerline (80) showing angle β (210) and one threaded bore (110).
Figure 10:
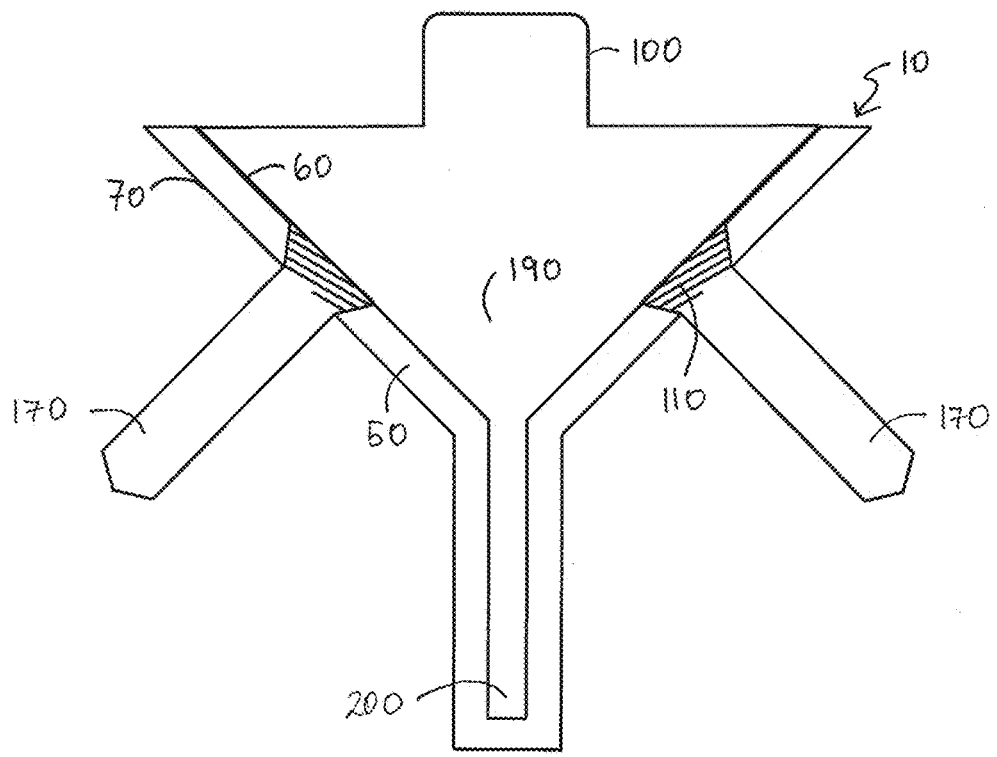
FIG. 10 shows aspects of a cross section of implant receiving apparatus (10) comprising a core (20), a funnel (190), a canal (200) extending from the centre of the funnel (190), a wall (50) comprising inner surface (60) and outer surface (70), threaded bores (110) and an implant engaging member (100) attached to the implant receiving apparatus.

According to another embodiment, and referring to FIG. 7, there is provided an implant receiving apparatus (10) comprising a core (20), the core defining a funnel (190) and a canal (200), the canal (200) extending from the centre of the funnel (190). The funnel and the canal are defined by a wall (50) comprising inner surface (60) and outer surface (70) and a centerline (80) extending centrally of and between the funnel (190) and canal (200), the size and shape of the core (20) defining a cavity to receive an implant engaging member (100, FIG. 10), wherein the wall comprises at least one threaded bore (110) for engaging a screw retainer, the bore traversing through the wall from the inner surface to the outer surface. This implant apparatus can be useful in places where there is not a sufficient amount of bone to install a conventional implant. For example, in subjects with severely resorbed mandibles, although uses other than for dental applications are contemplated. The design conserves bone since less bone is removed in the procedure to install the apparatus due to the funnel shape of the core with the relatively narrow canal. A fully cylindrical shape of the apparatus would involve the removal of more bone. The design allows for the firm attachment of the implant receiving apparatus and therefore the implant engaging member in areas where an inadequate or small amounts of bone are present. This embodiment is also contemplated for use in areas with normal bone presence.

In the above embodiment and referring to FIG. 7, the angle (210) formed between the wall (50) of the funnel and the centerline (80) is between zero and 90 degrees, preferably 30 degrees to 60 degrees, for example 30, 32, 34, 36, 38, 40, 42, 44, 46, 48, 50, 52, 52, 54, 56, 58 and 60 degrees. In one embodiment, 45 degrees is preferred. However, other angles including angles between the values listed above are also contemplated. Further, the angle may be defined by a range of any two of the values listed above. A funnel is meant to refer to a pipe or passage that is wider at the top and narrower at the bottom and therefore it is further contemplated that the funnel of the implant receiving apparatus may be cylindrical or substantially cylindrical in shape, for instance, having a circular cross-section, but other shapes are possible, for example, but not limited to oval, multilateral, frustoconical, lemniscate (figure-eight) cross-sectional and other volume-based configurations.

Figure 8:
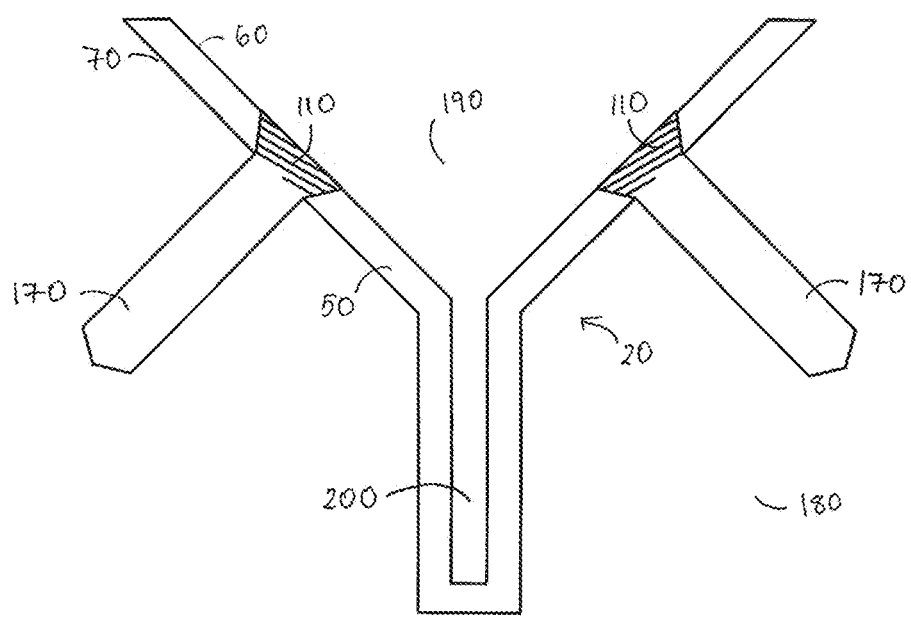
FIG. 8 shows aspects of a cross section of an implant receiving apparatus (10) comprising a core (20), a funnel (190), a canal (200) extending from the centre of the funnel (190), a wall (50) comprising inner surface (60) and outer surface (70), threaded bores (110) with medical grade screws (170) extending into the bone (180).
Figure 9:
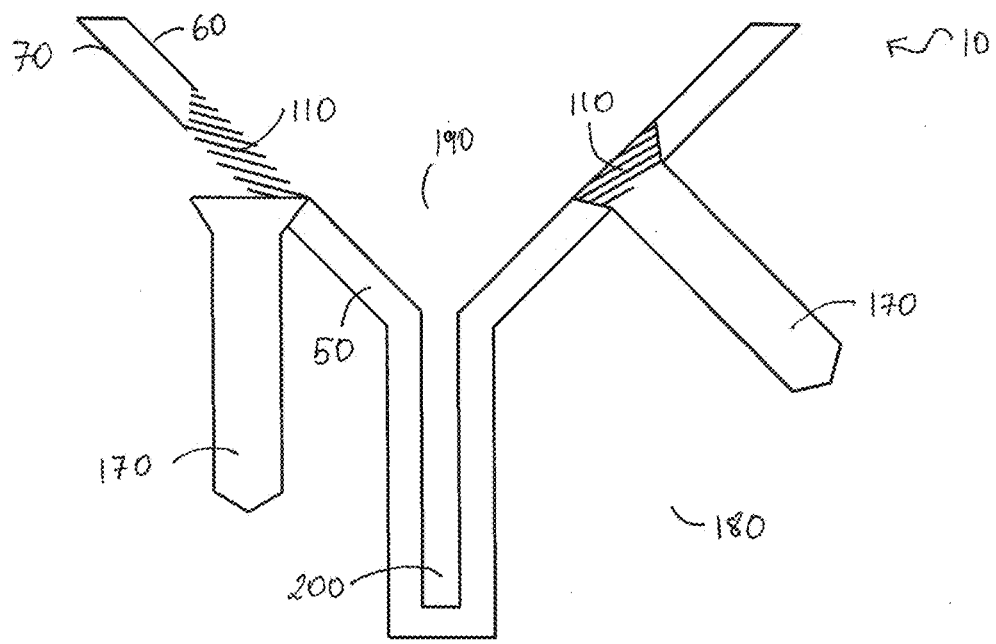
FIG. 9 shows aspects of a cross section of implant receiving apparatus (10) comprising a core (20), a funnel (190), a canal (200) extending from the centre of the funnel (190), a wall (50) comprising inner surface (60) and outer surface (70), threaded bore (110) at different angles with medical grade screws (170) extending into the bone (180) at different angles.

In embodiments wherein a plurality of threaded bores are employed, the bores may form the same or different angles with the centerline. Also possible, it is contemplated that a plurality of threaded bores may be positioned at different levels or depths in the wall or walls of the implant receiving apparatus. In one example referring to FIG. 8, the threaded bores (110) with screws (170) extend perpendicularly from the wall of the funnel and are flush with the inner surface (60) of the wall. In another example referring the FIG. 9, one threaded bore (110) is parallel to the centerline (80, FIG. 1) and the other screw is perpendicular to the wall. The orientation of the screws in these examples allows for the firm attachment of the implant receiving apparatus, resisting movement forces. In an embodiment where the implant receiving apparatus is for use in dentistry, the screws are oriented meseo-distially. In another embodiment where the implant receiving apparatus is for use in dentistry, the screws enter the apparatus at a level above the bone and under the gingival margin and anchor into the bone upon exit from the apparatus.

In the embodiments described above, the present invention also contemplates an implant engaging member that is attached to the implant receiving apparatus Collectively, the implant engaging member, implant receiving make up the implant system.

The implant engaging member may engage the implant receiving apparatus in a variety of ways, for example, but not limited to, the implant receiving apparatus may comprise a further threaded bore in a wall or surface of the cavity which permits the implant engaging member to be screwed into it. Alternatively, the implant receiving apparatus may comprise an extension or the like, for example, but not limited to a threaded post which may engage a threaded bore in the implant engaging member. Also possible, the implant engaging member may be sized to fit into the cavity of the implant receiving apparatus and the engaging member may be cemented, glued or otherwise affixed in place. As a further possibility, but not wishing to be limiting in any manner, the implant engaging member may comprise a portion which permits snap-fit attachment to the implant receiving apparatus. Combination of the above are also contemplated herein.

The present invention also contemplates one or more stints to assist in surgical implantation of the implant receiving apparatus. In an embodiment, there is provided a first stint having two fixed or interlocking guide cylinders. If for example, but not wishing to be limiting in any manner, interlocking guide cylinders are capable of receiving and guiding a three millimeter drill bit with guide holes that overlap at a dimension of 1.5 millimeters, this will create a lemniscate (figure-eight shaped) chamber with about 1.5 mm connecting area. The first stint then may be removed and a second stint may be inserted into the figure eight chamber. Again, without wishing to be limiting in any manner, one or more guide channels in the second stint may accept and guide a 1.5 mm drill bit at an angle, for example 45 degrees, or other appropriate or desired angle, through one end of the figure-eight surface. If required, a second hole may be made at about 45 degrees (or other appropriate or desired angle) at the opposite end through a second guide channel in the stint. The second stint can then be removed. Placement of the implant receiving apparatus, in this case, a lemniscates (figure-eight shaped) implant receiving apparatus is seated. A first screw may be inserted through one of the at least one threaded bores and screwed into place. A second screw is then inserted at the opposite end and the placement of this particular type of implant receiving apparatus is essentially complete.

The present invention also contemplates a hybrid of any of the embodiments described herein, for example incorporating any one or combination of the features recited. For example, but without being limiting, the back biting fins or projections (140) may be combined with the funnel (190) and canal (200) core.

The present invention also contemplates a kit comprising at least one of an implant receiving apparatus and one or more implant engaging members, stints, drill bits, medical grade screws, glue, cement or other component for affixing the implant engaging member to the implant receiving apparatus, directions for implanting the implant receiving apparatus, attaching the implant engaging member or any combination thereof.

The present invention has been described with regard to one or more embodiments. However, it will be apparent to persons skilled in the art that a number of variations and modifications can be made without departing from the scope of the invention as defined in the claims.

What is claimed is:

1. An implant receiving apparatus (10) comprising a core (20), the core defining a first end (30) and a second end (40), a wall (50) comprising an inner surface (60) and an outer surface (70), and a centerline (80) extending centrally of and between the first and second ends (30, 40), the size and shape of the core (20) defining a socket or cavity (90) adapted to receive an implant engaging member (100), wherein the wall comprises at least one threaded bore (110) for engaging a screw, the at least one threaded bore traversing through the wall from the inner surface to the outer surface;
   wherein an angle between an axis of the at least one threaded bore and the centerline is between 30 to 60 degrees; and
   wherein the inner surface of the wall comprises a projection, the at least one threaded bore traversing through at least part of the projection.

2. The apparatus of claim 1, wherein the wall is cylindrical, multilateral, frustoconical, oval or lemniscate in shape.

3. The apparatus of claim 1, wherein the wall comprises two or more threaded bores.

4. The apparatus of claim 1, wherein at least one threaded bore is positioned in an upper portion of the wall closer to the first end than the second end.

5. The apparatus of claim 1, wherein the at least one threaded bore is positioned in the wall at an angle to permit threading into the at least one threaded bore along the axis thereof without interference from the wall.

6. The apparatus of claim 1, wherein a surface of the projection comprises a groove allowing a screw head to be tightened flush with the surface of the projection.

7. The apparatus of claim 1, wherein the outer surface of the wall comprises a plurality of steps, back-biting fins, or extensions which resist removal of the apparatus during or after implantation.

8. The implant receiving apparatus of claim 1 further comprising an implant engaging member attached thereto.

9. The apparatus of claim 1, further comprising one or more screws sized to threadedly engage the at least one threaded bore.

10. An implant receiving system comprising the implant receiving apparatus of claim 1 and an implant engaging member.

11. The implant receiving system of claim 10, further comprising one or more medical grade screws.

12. A kit comprising the implant receiving apparatus of claim 1 and:
   a) one or more implant engaging members;
   b) one or more stints;
   c) one or more drill bits;
   d) one or more medical grade screws;
   e) one or more directions for implanting the implant receiving apparatus and an implant engaging member;
   f) one or more of glue or cement for affixing an implant engaging member to the implant receiving apparatus; or
   g) any combination of a)-f).

* * * * *